United States Patent [19]
Paterson et al.

[11] Patent Number: 5,763,482
[45] Date of Patent: Jun. 9, 1998

[54] BIOCIDAL COMPOSITION AND USE

[75] Inventors: Donald J. Paterson, Cordova, Tenn.; Howard A. Cash, Jacksonville, Fla.

[73] Assignee: BetzDearborn Inc., Trevose, Pa.

[21] Appl. No.: 821,746

[22] Filed: Mar. 20, 1997

[51] Int. Cl.⁶ .......................... A01N 33/12; A01N 37/34; A01N 43/40

[52] U.S. Cl. .................. 514/526; 514/358; 514/642; 514/643

[58] Field of Search ..................... 514/642, 643, 514/526, 358

[56] References Cited

U.S. PATENT DOCUMENTS

| | | | |
|---|---|---|---|
| 3,054,678 | 9/1962 | Michener et al. | 99/150 |
| 3,829,586 | 8/1974 | Sherma et al. | 424/329 |
| 3,833,731 | 9/1974 | Grier et al. | 424/304 |
| 4,655,815 | 4/1987 | Jakubowski | 71/67 |
| 5,034,405 | 7/1991 | Jakubowski | 514/369 |
| 5,444,088 | 8/1995 | Syrinek | 514/526 |
| 5,464,851 | 11/1995 | Morpeth | 514/373 |

FOREIGN PATENT DOCUMENTS 0482798  4/1992  European Pat. Off. .

*Primary Examiner*—Allen J. Robinson
*Attorney, Agent, or Firm*—Alexander D. Ricci; Richard A. Paikoff

[57] ABSTRACT

An antimicrobial composition and method for controlling the growth of microbes in an aqueous system is disclosed, the composition comprising an amount, effective for the purpose of a 2-bromo-2-(bromomethyl)-glutaronitrile and a quaternary ammonium compound.

7 Claims, No Drawings

BIOCIDAL COMPOSITION AND USE

BACKGROUND OF THE INVENTION

It is common for microorganisms in many aqueous environments to produce exopolysaccharide materials, commonly referred to as slime. This behavior manifests itself in not only natural waters, such as lagoons, lakes, and ponds, but also in confined waters, such as pools and in many industrial systems. Of particular interest are industrial applications, such as cooling water systems, air washer systems and pulp and paper mill systems. All of these environments possess conditions that are conducive to the growth and reproduction of slime forming bacteria. Uncontrolled, the formation of slime in closed systems, such as paper mills, and in once-through and recirculating cooling systems, is an expensive and constant problem.

In addition to the control of bacteria, there continues to be a need for less toxic materials that also control fungi in water systems. There are several active materials that control both bacteria and fungi, including methylene bisthiocyanate and bis(trichloromethyl) sulfone. These materials are reported to have aquatic toxicity profiles higher than the materials of the present invention.

Environmental regulations continue to place increasing emphasis on antimicrobial compositions that offer better mammalian and aquatic toxicological profiles. In addition, the environmental fate and effect of active materials continues to come under greater scrutiny.

DETAILED DESCRIPTION OF THE INVENTION

It has been discovered that a mixture of biocidal actives, specifically a 2-bromo-2-(bromomethyl)- glutaronitrile, also known as 1,2-dibromo-2,4-dicyanobutane (DBDCB) and quaternary ammonium compounds (Quats), provide a higher degree of antimicrobial activity than that of the individual ingredients comprising the mixture. The DBDCB compound is a particularly effective agent that is active against a broad spectrum of bacteria, yeast and fungi.

Examples of quaternary ammonium compounds include, but are not limited to, diethyl dodecyl benzyl ammonium chloride, octadecyl dimethyl benzyl ammonium chloride, dimethyl didecyl ammonium chloride, dimethyl didodecyl ammonium chloride, trimethyl tetradecyl ammonium chloride, trimethyl octadecyl ammonium chloride, trimethyl hexadecyl ammonium chloride, alkyl dimethyl benzyl ammonium chloride, cetyl pyridinium bromide, cetyl pyridinium chloride, dodecyl pyridinium chloride, and benzyl dodecyl bis(B-hydroxyethyl) ammonium chloride.

Because of the synergistic nature of this mixture of active compounds, it is therefore possible to produce an efficacious blend that, due to the enhanced activity, results in reduced treatment levels. Thus, this effectiveness may be capitalized on by using lower concentrations of each active ingredient.

In accordance with the present invention, the combined DBDCB:Quat treatment may be added to the desired aqueous system in need of biocidal treatment, in an amount of from about 0.5 to about 60 parts of the combined treatment to one million parts (by weight) of the aqueous medium. Preferably, about 0.5 to about 50 parts of the combined treatment per one million parts (by weight) of the aqueous medium is added.

The efficacy of the active materials and blends was determined using a dose protocol. The actives were evaluated in synthetic white water with pH values of 5.5 and 8.0. The materials were tested against an artificial bacterial consortium containing approximately equal numbers of six bacterial strains. Although the test strains are representative of organisms present in paper mill systems, the effect is not limited to these bacteria. Two of the strains were Klebsiella pneumoniae (ATCC13883) and Pseudomonas aeruginosa (ATCC 15442). The other four strains were isolated from papermill systems and have been identified as Curtobacterium flaccumfaciens, Burkholderia cepacia, Bacillus maroccanus, and Pseudomonas glathei. Each strain was incubated at 37° C. overnight, then suspended in sterile saline. Equal volumes of each strain were then combined to prepare the consortium. The bacterial consortium was distributed into the wells of a microtitration plate in the presence or absence of various concentrations of the active materials. The microtitration plates were incubated at 37° C. Optical density readings at 650 nm were taken initially ($t_0$) and after time ($t_4$) 4 hours of incubation.

The raw data was converted to "inhibition percentages" according to the following formula:

$$\% \text{ Inhibition} = [(a-b) \div a] \cdot 100$$

where $a$=(Optical Density (OD) of control at $t_n$) −(OD of control at $t_0$), and $b$=(OD of treatment at $t_n$)−(OD of treatment at $t_0$).

The inhibition values can be plotted versus dosage for each active and the particular blend. This results in a dose response curve from which the dosage to yield 50% inhibition ($I_{50}$) can be calculated. In the examples below, the $I_{50}$ values are expressed as parts per million (ppm) of active material.

The synergism index (SI) was calculated by the equations described by Kull, F. C., P. C. Eisman, H. D. Sylwestrowicz and R. L. Mayer (1961), *Applied Microbiology* 9, 538. The values are based on the amount needed to achieve a specified end point. The end point selected for this study was 50% inhibition.

$$SI@t_4=(Q_A \div Q_a)+(Q_B \div Q_b);$$

where $Q_A$=quantity of compound A in mixture, $Q_a$=quantity of compound A acting alone, $Q_B$=quantity of compound B in mixture, $Q_b$=quantity of compound B acting alone.

If SI is less than 1, synergism is demonstrated; if SI is greater than 1, antagonism is demonstrated; if SI=1, additive behavior is demonstrated.

TABLE I

DBDCB and Alkyl (40% $C_{12}$, 50% $C_{14}$, 10% $C_{16}$) Dimethyl Benzyl Ammonium Chloride (ADBAC)

| | pH 5.5 | | pH 8.0 | |
| --- | --- | --- | --- | --- |
| | $I_{50, ppm}$ | SI | $I_{50, ppm}$ | SI |
| DBDCB | 2.20 | | 2.30 | |
| 1 DBDCB: 1 ADBAC | 2.06 | 0.85 | 2.25 | 0.94 |
| ADBAC | 2.69 | | 2.69 | |
| DBDCB | 3.07 | | 2.79 | |
| 2 DBDCB: 1 ADBAC | 2.77 | 0.91 | 2.05 | 0.73 |
| ADBAC | 2.69 | | 2.78 | |

TABLE II

DBDCB and Lauryl Trimethyl Ammonium Chlorida (LTAC)

|  | pH 5.5 | | pH 8.0 | |
| --- | --- | --- | --- | --- |
|  | I$_{50, ppm}$ | SI | I$_{50, ppm}$ | SI |
| DBDCB | 2.380 | | 2.39 | |
| 2 DBDCB: 1 LTAC | 2.28 | 0.69 | 2.65 | 0.88 |
| LTAC | 14.12 | | 6.08 | |

TABLE III

DBDCB and Cetyl Trimethyl Ammonium Chloride (CTAC)

|  | pH 5.5 | | pH 8.0 | |
| --- | --- | --- | --- | --- |
|  | I$_{50, ppm}$ | SI | I$_{50, ppm}$ | SI |
| DBDCB | 3.19 | | 3.23 | |
| 2DBDCB: 1CTAC | 1.89 | 0.63 | 2.06 | 0.87 |
| CTAC | 2.66 | | 1.55 | |

TABLE IV

DBDCB and Cetyl Pyridinium Chloride (CPyrC)

|  | pH 5.5 | | pH 8.0 | |
| --- | --- | --- | --- | --- |
|  | I$_{50, ppm}$ | SI | I$_{50, ppm}$ | SI |
| DBDCB | 2.90 | | 1.99 | |
| 1DBDCB: 1CPyrC | 1.56 | 0.79 | 2.51 | 1.16 |
| CPyrC | 1.49 | | 2.36 | |
| DBDCB | 2.79 | | 2.27 | |
| 2DBDCB: 1CPyrC | 1.74 | 0.86 | 1.81 | 0.96 |
| CPyrC | 1.30 | | 1.39 | |

In accordance with Tables I–IV supra., unexpected results occurred more frequently within the product ratios of 2-bromo-2-(bromomethyl)-glutaronitrile (BBMG): Quat product of from about 2:1 to 1:20. Since the tested BBMG product was about 98% active, and the tested Quat products were about 80% active biocidal ingredient, this range translates to a range of BBMG:Quat (100% actives basis) of about 3:1 to 1:16. At present, it is preferred that the commercial product embodying the invention comprises a weight ratio of about 1:2 BBMG:Quat.

While this invention has been described with respect to particular embodiments thereof, it is apparent that numerous other forms and modifications of the invention will be obvious to those skilled in the art. The appended claims and this invention generally should be construed to cover all such obvious forms and moidications which are within the true spirit and scope of the present invention.

What is claimed is:

1. A method for controlling the growth of microbes in an aqueous system which comprises adding to said system an amount, effective for the purpose of a composition consisting essentially of a synergistic mixture of (a) a 2-bromo-2-(bromomethyl)-glutaronitrile and (b) a quaternary ammonium compound, wherein the weight ratio of (a) to (b) is from about 3:1 to 1:16.

2. The method as recited in claim 1 wherein said composition is added to said system in an amount of from about 0.5 to about 60 parts per million of said aqueous system.

3. The method as recited in claim 1 wherein the quaternary ammonium compound is selected from the group consisting of alkyl dimethyl benzyl ammonium chloride, lauryl trimethyl ammonium chloride, cetyl trimethyl ammonium chloride and cetyl pyridinium chloride.

4. The method as recited in claim 1 wherein said aqueous system comprises a cooling water system.

5. The method as recited in claim 1 wherein said aqueous system comprises a pulping and papermaking system.

6. An antimicrobial composition consisting essentially of synergistic effective amounts of (a) a 2-bromo-2-(bromomethyl)-glutaronitrile and (b) a quaternary ammonium compound, wherein the weight ratio of (a) to (b) is from about 3:1 to 1:16.

7. The composition as recited in claim 6 wherein the quaternary ammonium compound is selected from the group consisting of alkyl dimethyl benzyl ammonium chloride, lauryl trimethyl ammonium chloride, cetyl trimethyl ammonium chloride and cetyl pyridinium chloride.

* * * * *